(12) United States Patent
Luthra et al.

(10) Patent No.: US 7,115,249 B2
(45) Date of Patent: Oct. 3, 2006

(54) SOLID-PHASE ELECTROPHILIC FLUORINATION

(75) Inventors: Sajinder Kaur Luthra, London (GB); Frank Brady, London (GB); Harry John Wadsworth, Amerhsam (GB)

(73) Assignees: GE Healthcare Ltd., Buckinghamshire (GB); Hammersmith Imanet Ltd., London (GB)

( * ) Notice: Subject to any disclaimer, the term of this patent is extended or adjusted under 35 U.S.C. 154(b) by 188 days.

(21) Appl. No.: 10/482,542

(22) PCT Filed: Jun. 18, 2002

(86) PCT No.: PCT/GB02/02529

§ 371 (c)(1), (2), (4) Date: Dec. 24, 2003

(87) PCT Pub. No.: WO03/002489

PCT Pub. Date: Jan. 9, 2003

(65) Prior Publication Data

US 2004/0186312 A1 Sep. 23, 2004

(30) Foreign Application Priority Data

Jun. 29, 2001 (GB) ................................. 0115929.2

(51) Int. Cl.
*A61K 51/00* (2006.01)
*A61M 36/14* (2006.01)

(52) U.S. Cl. .................. 424/1.89; 424/1.11; 424/1.65; 424/1.81; 424/1.85; 424/9.1; 424/9.3

(58) Field of Classification Search ............... 424/1.11, 424/1.65, 1.81, 1.85, 1.89, 9.1, 9.3
See application file for complete search history.

(56) References Cited

FOREIGN PATENT DOCUMENTS

| JP | 08067657 | 12/1996 |
|----|----------|---------|
| WO | WO9400460 | 6/1994 |

OTHER PUBLICATIONS

Yun W, et.al. "Solid-phase synthesis of diaryl ketonoes through a three-component Stille coupling reaction" Tetrahedron Ltters, Elsevier Science Publishers, Amsterdam, NL, vol. 42, No. 2, Jan. 8, 2001 pp. 175-177.
Frank Forman, et.al. "Solid Phase Synthesis of Biaryls via the Stille Reaction" J. Org Chem., vol. 60, 1995, pp. 523-528.
Ding, et.al. "No-Carrier-Added (NCA) {18F} Fluorides via the nucleophilic Aromatic Substitution of Electron-Rich Aromatic Rings" J. Fluorine Chem., vol. 48, No. 2, 1990 pp. 189-205.

*Primary Examiner*—Dameron L. Jones
(74) *Attorney, Agent, or Firm*—Li Cai

(57) ABSTRACT

The invention relates to compounds of formula (I); wherein $R^1$ and $R^2$ independently selected from $C_{1-6}$ alkyl; $P^1, P^2, P^3$, and $P^4$ are each independently hydrogen or a protecting group; and their use in the preparation of $^{18}F$-labelled 6-L-fluorodopa

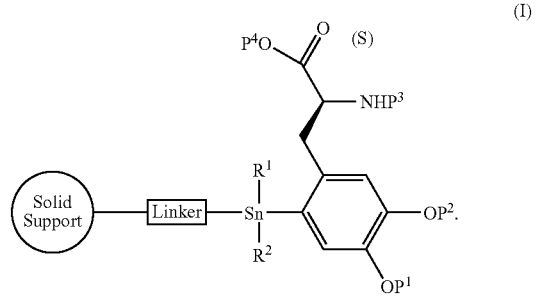

13 Claims, No Drawings

SOLID-PHASE ELECTROPHILIC FLUORINATION

This application is a filing under 35 U.S.C. § 371 and claims priority to international application number PCT/GB02/02529 filed Jun. 18, 2002, which claims priority to Great Britain application 0115929.2 filed Jun. 29, 2001.

The present invention relates to novel solid-phase processes for the production of radiolabelled tracers, in particular for the production of $^{18}$F-labelled 6-L-fluorodopa which may be suitable for use as a Positron•Emission Tomography (PET) tracer. The invention also comprises radiopharmaceutical kits using these novel processes.

The favoured isotope for PET, $^{18}$F, has a relatively short half-life of 110 minutes. $^{18}$F-labelled tracers, such as 6-L-$^{18}$F-fluorodopa (6-$^{18}$F-fluoro-3,4-dihydroxy-L-phenylalanine) ($^{18}$F-FDOPA), for PET therefore have to be synthesised and purified as rapidly as possible and shortly before clinical use. Standard synthetic methods for introducing fluorine-18 are relatively slow and require post-reaction purification (for example, by HPLC) which means that it is difficult to obtain the $^{18}$F-labelled tracer for clinical use in good radiochemical yield. $^{18}$F-FDOPA is widely used for monitoring cerebral dopamine metabolism.

The present invention provides solid-phase processes for producing $^{18}$F-labelled tracers quickly yet avoiding time-consuming purification steps, such that the resultant $^{18}$F-labelled tracer is suitable for use in PET. The solid-phase methods also lend themselves to automation with advantages of ease of production and greater throughput. The invention also comprises radiopharmaceutical kits which use such processes and thus provide the radiopharmacist or clinician with a convenient means of preparing an $^{18}$F-labelled tracer.

Thus in a general aspect, the present invention provides a process for the production of 6-L-$^{18}$F-fluorodopa ($^{18}$F-FDOPA) which comprises treatment of a solid support-bound FDOPA precursor of formula (I):

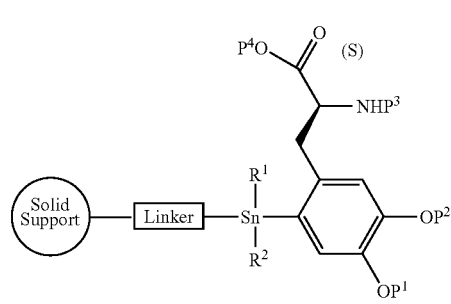

(I)

wherein $R^1$ and $R^2$ independently selected from $C_{1-6}$ alkyl; $P^1$, $P^2$, $P^3$, and $P^4$ are each independently hydrogen or a protecting group;
with a source of $^{18}$F, suitably $^{18}$F$_2$, $^{18}$F—CH$_3$COOF or $^{18}$F—OF$_2$;

to give the labelled tracer of formula (II)

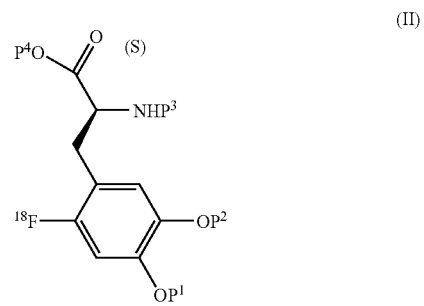

(II)

wherein $P^1$, $P^2$, $P^3$, and $P^4$ are each independently hydrogen or a protecting group; optionally followed by:
(i) removal of excess fluorinating agent and $^{18}$F$^-$ions produced in the generation of the fluorinating agent or in the reaction; and/or
(ii) removal of any protecting groups; and/or
(iii) removal of organic solvent; and/or
(iv) formulation of the resultant compound of formula (II) as an aqueous solution.

In a preferred aspect, $R^1$ and $R^2$ are both methyl.

In the compounds of formula (I) and throughout this specification unless otherwise stated, the "Solid Support" may be any suitable material which is insoluble in any solvents to be used in the process but to which the "Linker" and/or FDOPA precursor can be covalently bound. Examples of suitable solid support include polymers such as polystyrene (which may be block grafted, for example, with polyethylene glycol), polyacrylamide, and polypropylene or glass or silicon suitably coated with such a polymer. The solid support may be in the form of small discrete particles such as beads or pins, or as a coating on the inner surface of a cartridge or on a microfabricated vessel.

In the compounds of formula (I) and throughout this specification, the "Linker" may be any suitable organic group which serves to space the reactive site sufficiently from the solid support structure so as to maximise reactivity. Suitably, the Linker comprises an organic group of from 1 to 12 carbon atoms and from 0 to 6 heteroatoms selected from oxygen, nitrogen, and sulphur. Examples of such linkers are well known to those skilled in the art of solid-phase chemistry, but include:

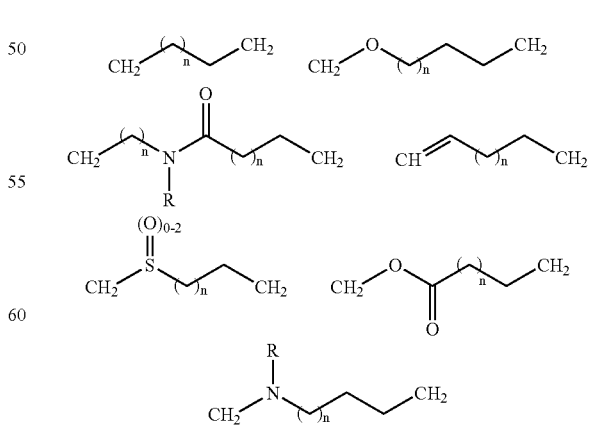

wherein n is 0 to 10 and R is $C_{1-6}$ alkyl.

In a preferred aspect of the invention, the Linker is a methoxy-$C_{1-6}$alkyl group, most suitably, a methoxypropyl group.

As would be apparent to the person skilled in the art, it may be necessary to protect functional groups to avoid unwanted reactions in the tracer. Such protection may be achieved using standard methods of protecting group chemistry. After the radiolabelling is complete, any protecting groups may be removed by simple procedures which are also standard in the art. Suitable protection and deprotection methodologies may be found, for example, in Protecting groups in organic synthesis, Theodora W. Greene and Peter G. M. Wuts, published by John Wiley & Sons inc, 605 third avenue, New York, N.Y. 10158-0012.

In each aspect of the invention, the acid functionality of the FDOPA precursor is conveniently protected as an ester, suitably $C_{1-6}$ alkyl ester, the phenol functionalities of the FDOPA precursor are conveniently protected as carbonate ester, suitably $C_{1-6}$ alkyl carbonate esters and the amine functionality of the FDOPA precursor is conveniently protected as an amide, suitably a $C_{1-6}$ alkyl amide or urethane. In a preferred aspect, both $P^1$ and $P^2$ are t-butoxycarbonyl, $P^3$ is formyl or t-butoxycarbonyl, and $P^4$ is ethyl. The protecting groups may be conveniently removed by hydrolysis (e.g. acid hydrolysis), for example, at elevated temperature, such as 50° C. to 130° C., in the presence of aqueous acid such as aqueous hydrobromic acid. Such acid hydrolysis may be followed by a neutralisation step, using an inorganic base, for example, aqueous sodium hydroxide. Such deprotection may also be effected using solid supported acid catalysts that render the need for post-deprotection neutralisation unnecessary. One example of such a solid supported acid catalyst would be a Dowex Sulphonate resin. An aqueous solution of the optionally protected F-18 DOPA of formula (II) at elevated temperature, such as 50° C. to 130° C., would be treated with the resin to effect deprotection.

Treatment of the compound of formula (I) with $^{18}F$ may be effected by treatment with any suitable source of $^{18}F$, such as $^{18}F_2$, $^{18}F$—$CH_3COOF$, or $^{18}F$—$OF_2$, in the presence of a suitable organic solvent, suitably a chlorofluorocarbon or fluorocarbon, such as trichlorofluoromethane, at a non-extreme temperature, for example, −10° C. to 60° C., preferably at ambient temperature. On completion of the reaction, the $^{18}F$-labelled tracer of formula (II) dissolved in the solvent is conveniently separated from the solid-phase by filtration. The $^{18}F_2$ may be produced, for example, by the 20Ne(d,α) $^{18}F$ reaction using the 13.5 Mev deuterons of the Rossendorf cyclotron U-120 with Ne+0.2% $F_2$ (100 umol) as target gas. Alternatively, the $^{18}F_2$ may be produced by the $^{18}O_2$ (p,n) $^{18}F$ reaction, using 11 Mev protons from a cyclotron (A. J. Bishop et al, J. Nucl. Med., 32:1010(1991)).

Any excess fluorinating agent or $^{18}F^-$ ions produced in the generation of the fluorinating agent or in the reaction and may be removed from the solution of $^{18}F$-tracer of formula (II) by any suitable means, for example by passing through a column of sodium sulphite and silica gel in a suitable solvent, suitably a chlorofluorocarbon or a chlorocarbon, such as chlorofluoromethane or methylene chloride.

Any organic solvent may be removed by any standard method such as by evaporation at elevated temperature in vacuo or by passing a stream of an inert gas such as nitrogen, or argon over the solution.

Before use of the $^{18}F$-labelled DOPA, it may be appropriate to formulate it, for example as an aqueous solution by dissolving the $^{18}F$-labelled tracer in sterile isotonic saline, which may contain up to 10% of a suitable organic solvent such as ethanol, or a buffered solution such as phosphate buffer. Other additives may be added, for example, a radiostabiliser such as ascorbic acid, or a bacteriostat such as 4-hydroxybenzoic acid $C_{1-4}$ alkyl esters.

In a more specific aspect, the present invention provides a process for the production of 6-L-$^{18}F$-fluorodopa ($^{18}F$-FDOPA) which comprises treatment of a solid support-bound FDOPA precursor of formula (Ia):

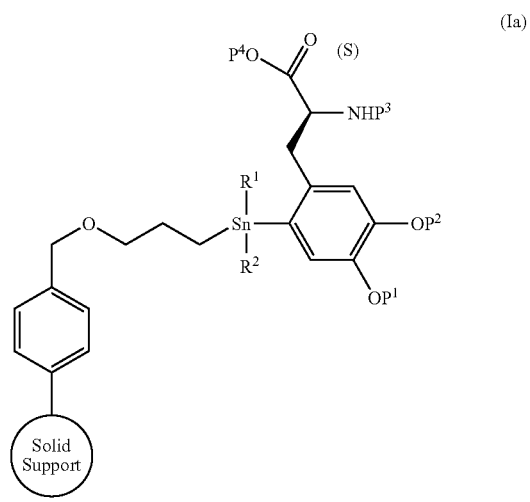

(Ia)

wherein $R^1$ and $R^2$ independently selected from $C_{1-6}$ alkyl and are preferably both methyl;
$P^1$, $P^2$, $P^3$, and $P^4$ are each independently hydrogen or a protecting group;
with a source of $^{18}F$, suitably $^{18}F_2$, $^{18}F$—$CH_3COOF$, or $^{18}F$—$OF_2$;

to give the labelled tracer of formula (II):

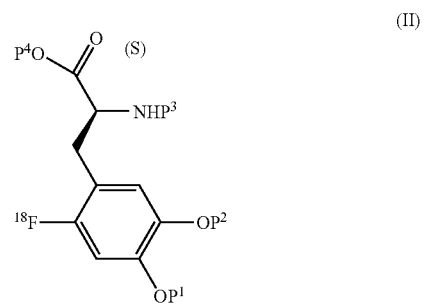

(II)

wherein $P^1$, $P^2$, $P^3$, and $P^4$ are each independently hydrogen or a protecting group; optionally followed by
(i) removal of excess fluorinating agent and $^{18}F^-$ ions produced in the generation of the fluorinating agent or in the reaction; and/or
(ii) removal of any protecting groups such that $P^1$, $P^2$, $P^3$, and $P^4$ are each hydrogen; and/or
(iii) removal of organic solvent; and/or
(iv) formulation of the resultant compound of formula (II) as an aqueous solution.

The solid support-bound precursor of formula (Ia) may be prepared from commercially available starting materials as outlined in Scheme 1 or Scheme 2.

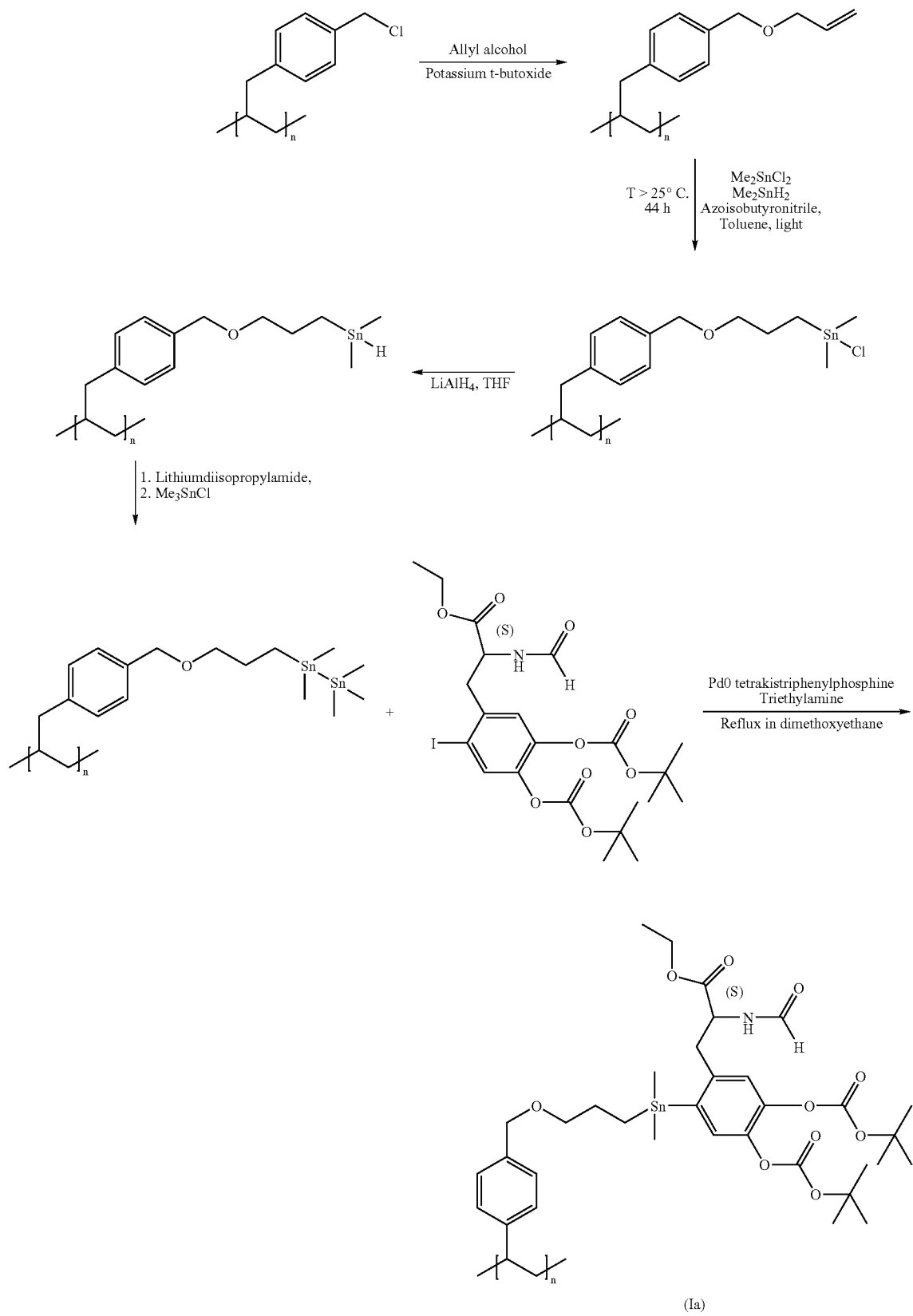

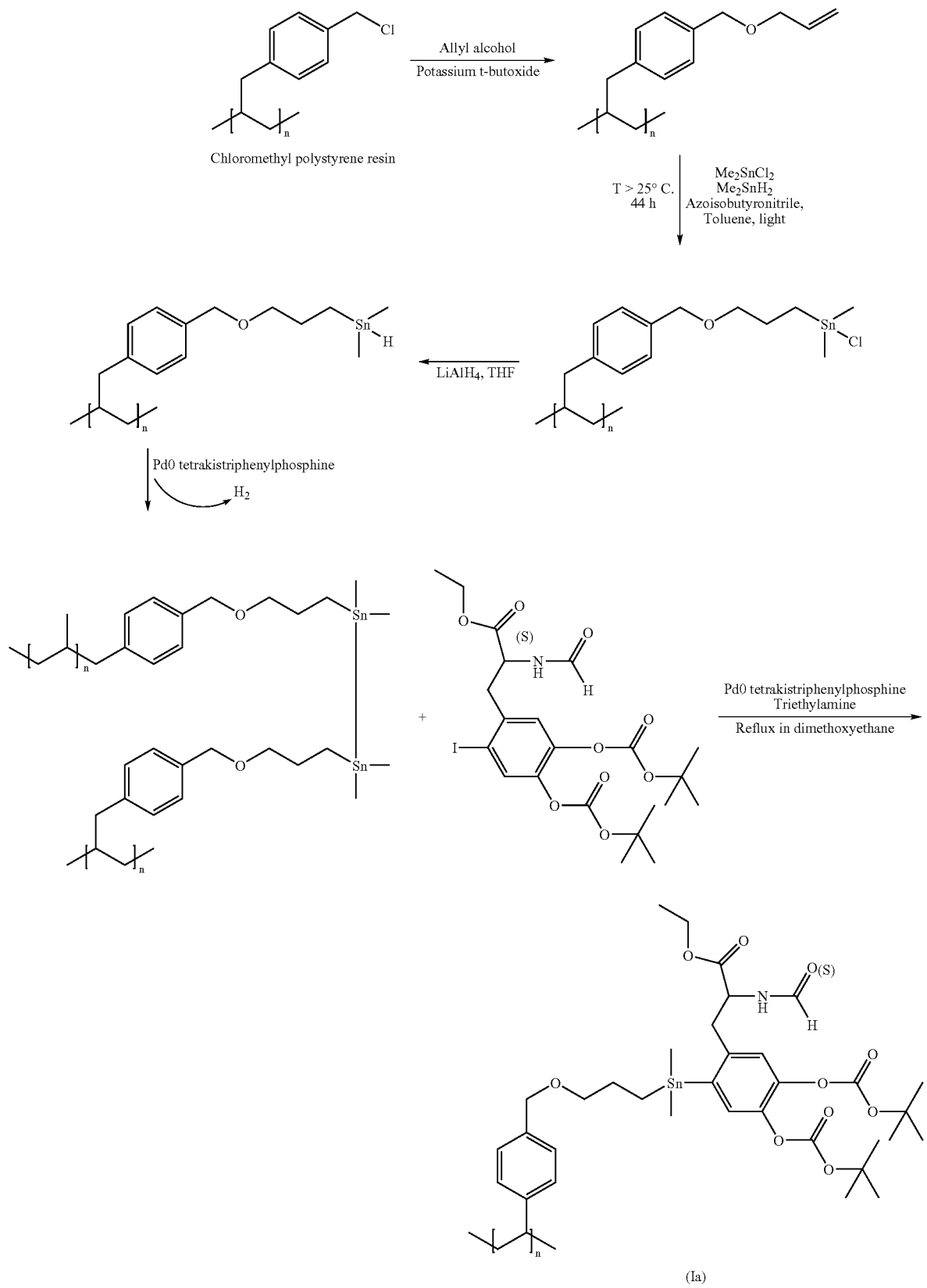

Compounds of formulae (I) and (Ia) are novel and thus constitute further aspects of the present invention.

According to a further aspect, there is provided a process for the preparation of a compound of formula (I) which comprises reaction of a compound of formula (III)

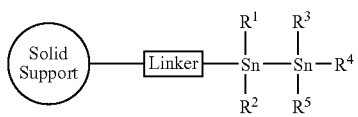
(III)

wherein either:

$R^1$, $R^2$, $R^3$, $R^4$, and $R^5$ are each independently selected from $C_{1-6}$ alkyl and are each preferably methyl; or $R^1$, $R^2$, $R^3$, and $R^5$ are each independently selected from $C_{1-6}$ alkyl and are each preferably methyl and $R^4$ is

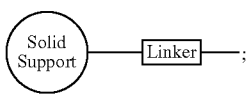;

with a compound of formula (IV)

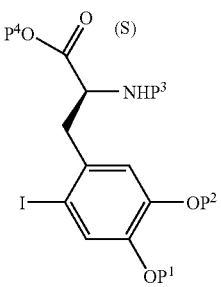
(IV)

wherein $P^1$, $P^2$, $P^3$, and $P^4$ are each independently hydrogen or a protecting group. This reaction is suitably carried out in the presence of a catalyst, suitably a palladium catalyst, such as $Pd(0)(PR'_3)_4$ wherein R' is selected from phenyl, phenyl substituted with 1 to 4 organic groups, $C_{1-6}$ alkyl, or $C_{1-6}$ alkoxymethyl, a preferred catalyst is palladium (0) tetrakistriphenylphosphine, and in the presence of an organic base such as a trialkylamine, for example triethylamine, in a suitable solvent such as dimethoxyethane, at elevated temperature, typically at reflux.

In a more particular aspect of the invention, there is provided a process for the preparation of a compound of formula (Ia) which comprises reaction of a compound of formula (IIIa)

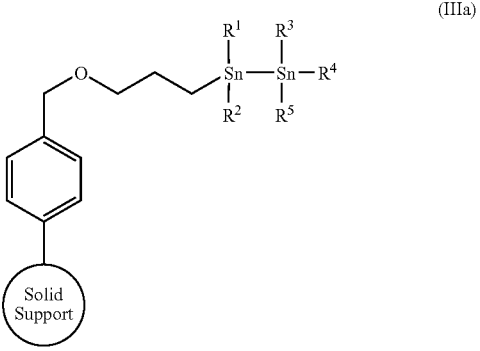
(IIIa)

wherein either:

$R^1$, $R^2$, $R^3$, $R^4$, and $R^5$ are each independently selected from $C_{1-6}$ alkyl and are preferably each methyl; or $R^1$, $R^2$, $R^3$, and $R^5$ are each independently selected from $C_{1-6}$ alkyl and are each preferably methyl and $R^4$ is

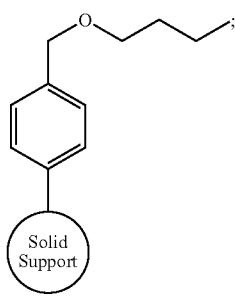;

with a compound of formula (IV) as defined above. This reaction is suitably carried out in the presence of a catalyst, suitably a palladium catalyst, such as $Pd(0)(PR'_3)_4$ wherein R' is selected from phenyl, phenyl substituted with 1 to 4 organic groups, $C_{1-6}$ alkyl, or $C_{1-6}$ alkoxymethyl, a preferred catalyst is palladium (0) tetrakistriphenylphosphine, and in the presence of an organic base such as a trialkylamine, for example triethylamine, in a suitable solvent such as dimethoxyethane, at elevated temperature, typically at reflux.

As would be appreciated by the person skilled in the art, this chemistry may be applied to preparation of a solid support-bound precursor for tracers other than FDOPA. Accordingly, in a more general aspect of the invention, there is provided a process for the preparation of a compound of formula (V)

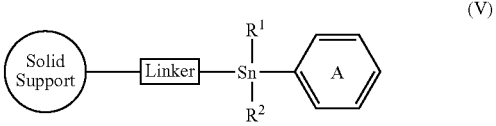
(V)

wherein R¹ and R² independently selected from $C_{1-6}$ alkyl and are preferably both methyl, and phenyl ring "A" is optionally substituted with 1 to 5 organic groups; which comprises:

reaction of a compound of formula (III)

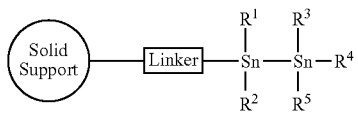
(III)

wherein either:

$R^1$, $R^2$, $R^3$, $R^4$, and $R^5$ are each independently selected from $C_{1-6}$ alkyl and are preferably each methyl; or $R^1$, $R^2$, $R^3$, and $R^5$ are each independently selected from $C_{1-6}$ alkyl and are each preferably methyl and $R^4$ is

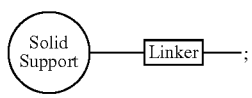

with the corresponding compound of formula (VI)

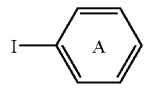
(VI)

wherein phenyl ring "A" is substituted as described in the compound of formula (V). This reaction is suitably carried out in the presence of a catalyst, suitably a palladium catalyst, such as $Pd(0)(PR'_3)_4$ wherein R' is selected from phenyl, phenyl substituted with 1 to 4 organic groups, $C_{1-6}$alkyl, or $C_{1-6}$alkoxymethyl, a preferred catalyst is palladium (0) tetrakistriphenylphosphine, and in the presence of an organic base such as a trialkylamine, for example triethylamine, in a suitable solvent such as dimethoxyethane, at elevated temperature, typically at reflux.

In formula (V) and in formula (Va) below, the "organic groups" which optionally form substituents on phenyl ring "A" are suitably independently selected from (a) halo, cyano, hydroxy, $C_{1-6}$ alkoxy, $C_{1-6}$ carboxylic acid or ester, an amine or amide group; and (b) saturated or unsaturated straight or branched chain, or cyclic systems comprising from 1 to 12 carbon atoms and 0 to 4 heteroatoms each of which may be optionally substituted by the groups listed in (a).

In a preferred embodiment of this aspect of the invention, there is provided a process for the preparation of a compound of formula (Va)

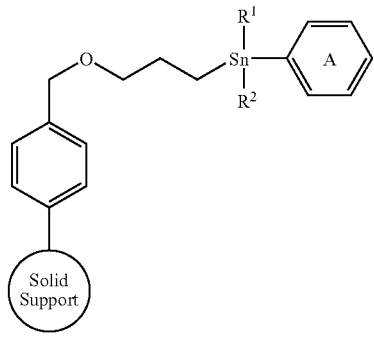
(Va)

wherein R¹ and R² independently selected from $C_{1-6}$ alkyl and are preferably both methyl and phenyl ring "A" is optionally substituted with 1 to 5 organic groups; which comprises:

reaction of a compound of formula (IIIa):

(IIIa)

wherein either:

$R^1$, $R^2$, $R^3$, $R^4$, and $R^5$ are each independently selected from $C_{1-6}$ alkyl and are preferably each methyl; or $R^1$, $R^2$, $R^3$, and $R^5$ are each independently selected from $C_{1-6}$ alkyl and are each preferably methyl and $R^4$ is

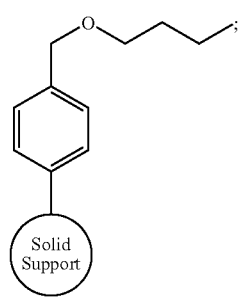

with a compound of formula (VI) as defined above. This reaction is suitably carried out in the presence of a catalyst, suitably a palladium catalyst, such as $Pd(0)(PR'_3)_4$ wherein R' is selected from phenyl, phenyl substituted with 1 to 4 organic groups, $C_{1-6}$alkyl, or $C_{1-6}$alkoxymethyl, a preferred catalyst is palladium (0) tetrakistriphenylphosphine, and in the presence of an organic base such as a trialkylamine, for example triethylamine, in a suitable solvent such as dimethoxyethane, at elevated temperature, typically at reflux.

In a particular example of the above aspects, the compound of formula (VI) is 2-beta-carbomethoxy-3-beta-(4-iodophenyl)-8-(3-fluoropropyl)-nortropane:

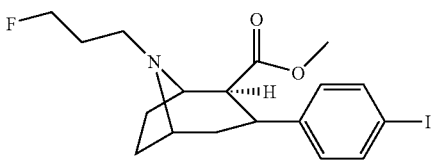

As described above, the advantages of such solid-phase processes for preparation of $^{18}$F-labelled tracers include the relative speed of the process, simplified purification methods and ease of automation—all of which mean that the processes are suitable for preparation of $^{18}$F-labelled tracers for use in PET. Accordingly, the present invention provides the use of a process for the manufacture of a $^{18}$F-labelled tracer of formula (II) for use in PET.

Conveniently, the solid support bound DOPA of formula (I) could be provided as part of a kit to a radiopharmacy. The kit may contain a cartridge which can be plugged into a suitably adapted automated synthesiser. The cartridge may contain, apart from the solid support-bound FDOPA precursor, a column to remove unwanted fluoride ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customers requirements for radioactive concentration, volumes, time of delivery etc.

Conveniently, all components of the kit are disposable to minimise the possibilities of contamination between runs and will be sterile and quality assured.

The invention further provides a radiopharmaceutical kit for the preparation of $^{18}$F-FDOPA for use in PET, which comprises:
(i) a vessel containing a compound of formula (I) or (Ia); and
(ii) means for eluting the vessel with a source of $^{18}$F; and optionally
(iii) a cartridge for removal of excess fluorinating agent and $^{18}$F$^-$ ions; and optionally
(iv) a cartridge for solid-phase deprotection of the resultant product of formula (II).

The invention further provides a cartridge for a radiopharmaceutical kit for the preparation of $^{18}$F-FDOPA for use in PET which comprises:
(i) a vessel containing a compound of formula (I) or (Ia); and
(ii) means for eluting the vessel with a source of $^{18}$F.

In a further aspect of the invention, there is provided a method for obtaining a diagnostic PET image which comprises the step of using a radiopharmaceutical kit or a cartridge for a radiopharmaceutical kit as described above.

The invention will now be illustrated by way of the following Examples. Throughout the Examples, abbreviations used are as follows:
AcCN: Acetonitrile
AIBN: 2,2,-azobis(2-methylpropionitrile)
Boc: tert-Butoxycarbonyl
DCM: Dichloromethane
DMF: Dimethyformamide
Et: Ethyl
EtOH: Ethanol
h: hour(s)
HPLC: High-Performance-Liquid-Chromatography
I-DOPA: N-Formyl-3,4-di-t-butoxycarbonyloxy-6-Iodo-L-phenylalanine ethyl ester
MeOH: Methanol
min: minute(s)
NaH: Sodium hydride
N$_2$: Nitrogen
LiAlH$_4$: Lithiumaluminium hydride
Pd(PPh$_3$)$_4$: Tetrakistriphenylphosphine palladium
THF: Tetrahydrofuran
UV: Ultraviolet

EXAMPLE 1

Preparation of Resin Bound Dimethyl Tin Protected Dopa

EXAMPLE 1(i)

Preparation of a Polymer Bound Allyl Ether from Merrifield Resin

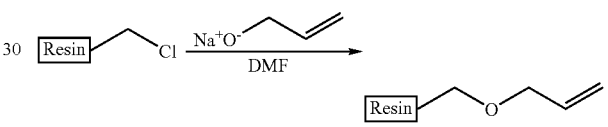

Starting material: Merrifield resin HL (100–200 mesh) Polystyrene crosslinked with 2% Divinylbenzene (Novabiochem) Substitution: 1.6 mMol/g. Method used was analogous to that described in Zhu et al (2000). Tetrahedron Lett., 41, 9219.

A solution of a 60% NaH dispersion in oil (Aldrich) (8 g, 0.2 Mol) in dry DMF (60 mL) was cooled to 0° C. under N$_2$. To this solution allyl alcohol (12.2 mL, 0.18 mMol) was added carefully over 30 min. under N$_2$. This solution was allowed to reach room temperature. After two hours stirring the alcoholate solution was transferred via cannula to a slurry containing Merrifield resin (10 g, 0.016 Mol) in dry DMF (40 mL) under N$_2$. The slurry was then very gently stirred with a small magnetic stirrer for 20 h at 50° C. The reaction was quenched with EtOH to remove the excess of NaH. The resin is then washed with water, EtOH, MeOH, Acetone, DMF and DCM and dried in a vacuum oven at 40° C. for 16 hours.

EXAMPLE 1(ii)

Hydrostannation of the Polymer Bound Allyl Ether

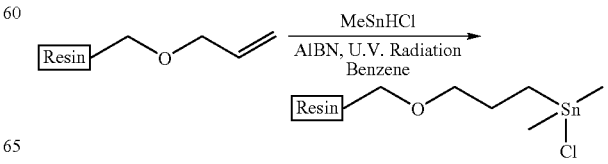

The procedure first introduced by Neumann et al. (J. Pedain. (1962). Tetrahedron Lett., 3, 2461) that involves the use of dimethylmonochlorotin hydride was used. This was obtained in situ by halogen exchange between dimethyltindihydride and dimethyltindichloride (A. K. Sawyer, H. G. Kuivila. (1961). Chem. Ind., 260). For the preparation of dimethyltindihydride the procedure published by Kuivila et al. involving the use of tributyltinhydride as reducing agent was used ((1971). J. Org. Chem., 36 (15), 2083).

Step 1. Preparation of Dimethyltindihydride

A 250 mL three necked flask equipped with a magnetic stirrer, addition funnel and an Argon balloon equipped with a tap was charged with dimethyltindichloride (14 g., 0.052 Mol). Glass tubing was used to connect the flask consecutively to two receiving vessels cooled to −70° C. and to −180° C. respectively. Tributyltinhydride (66 mL, 0.24 Mol) was carefully added. Pressure in the system was reduced slowly to 20 mm Hg with a water pump. The reaction vessel was heated to ca. 75° C. for 30 min. until no more bubbling in the solution was observed. Approximately 7 mL of the product as a colorless liquid was obtained in the first collection vessel at −70° C. This was used immediately for the following reaction without further characterization. All processes were carried out in an Argon atmosphere.

Step 2. Hydrostannation

Dimethyltindihydride (2.1 mL, 3.1 g, 0.02 Mol) was added with a syringe to a 250 mL two necked flask charged with a suspension of polymer (as prepared in Example 1(i)) (5 g, approx. 0.008 Mol), dimethyltindichloride (4.4 g., 0.02 Mol) and AIBN (100 mg, 0.6 mMol) in dry benzene (60 mL). The suspension was irradiated with an UV Lamp positioned at about 25 cm. from the flask. A very gentle stirring with a magnet stirrer was applied. Another portion of a solution of AIBN (100 mg, 0.6 mMol) in benzene (4 mL) was added to the suspension after 14 h. The temperature was maintained constant with a water bath in a Dewar vessel. All the processes were carried out in an Argon atmosphere. Total reaction time was 48 h. The resin was then washed thoroughly with toluene, methanol and acetone (approximately 100 mL each, with shaking of the suspension for 5 min., 3 cycles) and dried after a final wash of ether in a vacuum oven at 40° C. for 48 h. A grey resin (6.5 g) was obtained.

Note: A long wave 100 W Ultraviolet Lamp (UVP: model B100AP, Fisher catalogue: LCF461-020V) was used.

EXAMPLE 1(iii)

Reduction of Polymer Bound Tin Chloride to the Corresponding Tin Hydride

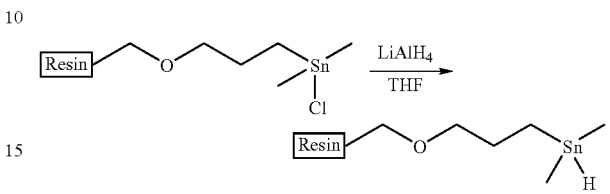

A suspension of resin (as prepared in Example 1(ii)) (2 g, approx. 2.4 mMol) in freshly distilled THF (60 mL) in a 250 mL two-necked flask with a magnetic stirrer was cooled to 0° C. with an ice bath. A solution 1M in THF of lithium aluminium hydride (Aldrich) (12 mL, 12 mMol) was then slowly added to the suspension while a very gentle stirring was applied. A bubbling coming from the resin bead was observed. The reaction was allowed to warm to room temperature for 2 h. After that the resin was washed thoroughly with dry THF (100 mL, shaking for approx. 5 min., 5 cycles) and dried with a stream of Argon. A gray polymer (1.8 g resin) was recovered.

EXAMPLE 1(iv)

Solid-phase Palladium Mediated Stannylation of I-Dopa

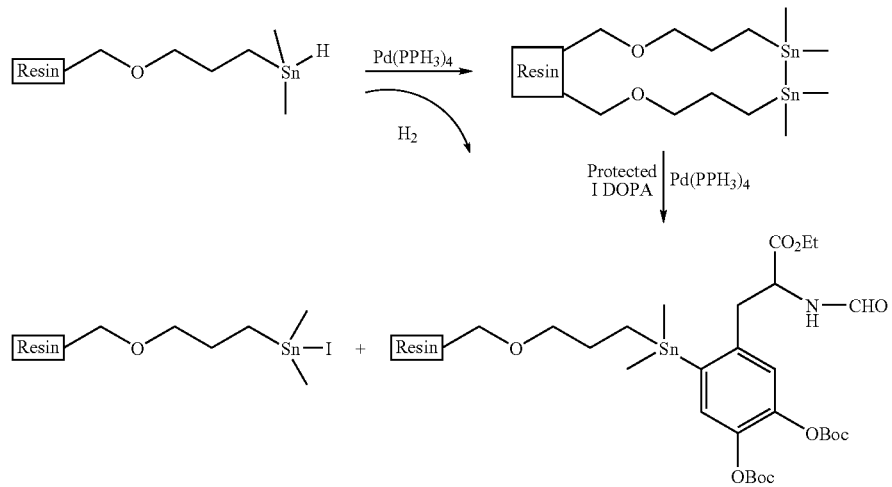

The resin (as prepared in Example 1(iii)) (500 mg, approximately 0.6 mMol) was suspended in freshly distilled (CaH$_2$) and deoxygenated (Argon bubbling) 1–4 dioxane (15 mL) for 5 min. The catalyst (Pd(PPh$_3$)) (208 mg; 0.18 mMol) was then added. The yellow mixture was stirred gently for 2 hours until no more H$_2$ evolution was observed. Di-O-t-butoxycarbonyl-6-iodo, N-formyl-Dopa ethyl ester (ABX, Radeberg, Germany) (1.2 g, 2 mMol) was then added. The mixture turned orange almost immediately and a fine white precipitate was formed. The solvent was refluxed for 6 h. Thereafter the mixture was allowed to cool down, after which the resin was thoroughly washed with freshly distilled dioxane (30 ml, with shaking for about 5 min, 5 cycles). The resin was then dried first with a stream of Argon for 10 min. and later in a vacuum oven at 40° C. for 16 h. A gray polymer (605 mg) was recovered.

COMPARATIVE EXAMPLE 2

Cleavage of I-DOPA From Resin Bound Dimethyl Tin Protected Dopa Via Halodestannylation with Iodine Aliquots of 20 mg of resin (prepared as described in Example 1(iv)) (approx. 0.012 mMol) were suspended in dry dioxane (in 1 ml) in a test tube for 5 min. To the suspension iodine (25 mg, 0.1 mMol) was added and dissolved by gently shaking of the tube. After the reaction (30 min, 5 h. or 16 h) 1 mL of diethyl ether was added. The suspension was then washed with a solution 0.5N of sodium metabisulfite (1 ml). The organic layer (1 mL) was extracted with a pasteur pipette and evaporated in vacuum. The extract was then dissolved in AcCN (1 ml) and analyzed by HPLC. Two aliquots of resin were exactly handled without addition of iodine as a control.

Estimation of I-DOPA Release

The amount of I-DOPA released was determined by LC-UV-(MS).

Maximal theoretical substitution: 0.4 mMol/g (Assuming a 100% yield in all steps from the tin chloride resin), thus maximum yield from 20 mg resin: (0.008 mMol) is approximately 5 mg.

| Experiment | Area | Concentration mg/mL | DOPA released mg | Yield % |
|---|---|---|---|---|
| t = 30 min. | 657 | 0.16 | 0.16 | 3.2 |
| t = 5 h | 412 | 0.098 | 0.098 | 1.96 |
| t = 16 h (1st extraction) | 31 | 7.4 * 10$^{-3}$ | 7.4 * 10$^{-3}$ | 0.15 |
| t = 16 h (2nd extraction) | 208 | 0.05 | 0.05 | 1 |
| Control1 (30 min) | 6.4 | 1.5 * 10$^{-3}$ | 1.5 * 10$^{-3}$ | 0.03 |
| Control2 (16 h) | 12 | 2.8 * 10$^{-3}$ | 2.8 * 10$^{-3}$ | 0.06 |
| Blank | — | — | — | — |

The results suggest that the addition of iodine promotes a significant release of I-DOPA from the resin.

EXAMPLE 3

Cleavage [$^{18}$F]-FDOPA from Resin Bound Dimethyl Tin Protected Dopa via Halodestannylation with [$^{18}$F]-fluorine Radiolabelled [$^{18}$F]F$_2$ is produced via $^{18}$O (p,n) $^{18}$F reaction and passed directly from the cyclotron and bubbled through a suspension of the resin (prepared as described in Example 1(iv) in Freon-11 at room temperature for a period of 2–3 minutes. The suspension is filtered and the Freon-11 removed by evaporation. The residue is re-dissolved in methanol and transferred to HPLC for analysis. A portion of the decayed material is analysed by mass spectrometry and NMR.

The invention claimed is:

1. A process for the production of 6-L-$^{18}$F-fluorodopa ($^{18}$F-FDOPA) which comprises treatment of a solid support-bound FDOPA precursor of formula (I):

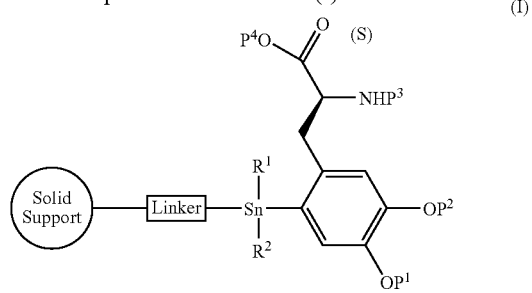

(I)

wherein R$^1$ and R$^2$ independently selected from C$_{1-6}$ alkyl;
P$^1$, P$^2$, P$^3$, and P$^4$ are each independently hydrogen or a protecting group;
with a source of $^{18}$F selected from the group consisting of $^{18}$F$_2$, $^{18}$F—CH$_3$COOF and $^{18}$F—OF$_2$;
to give the labelled tracer of formula (II)

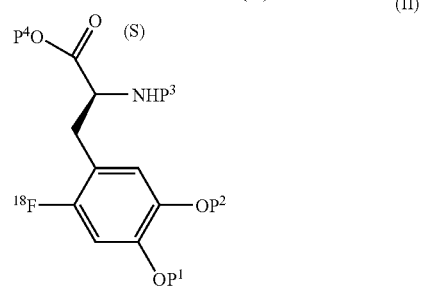

(II)

wherein P$^1$, P$^2$, P$^3$, and P$^4$ are each independently hydrogen or a protecting group;
optionally followed by:
(i) removal of excess fluorinating agent and $^{18}$F$^-$ ions produced in the generation of the fluorinating agent or in the reaction of a compound of formula (I) with a source of $^{18}$F; and/or
(ii) removal of any protecting groups; and/or
(iii) removal of organic solvent; and/or
(iv) formulation of the resultant compound of formula (II) as an aqueous solution.

2. A process for the production of 6-L-$^{18}$F-fluorodopa ($^{18}$F-FDOPA) according to claim 1 which comprises treatment of a solid support-bound FDOPA precursor of formula (Ia):

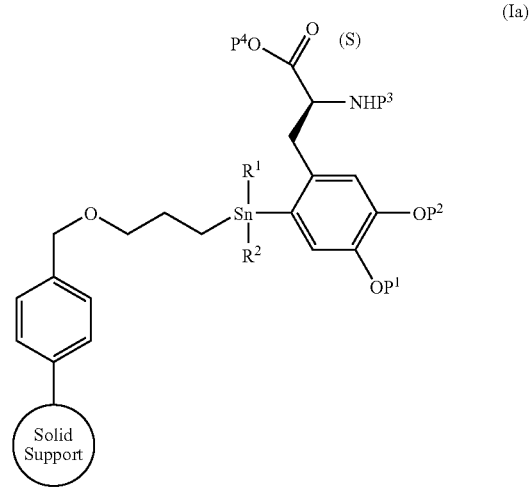

(Ia)

wherein R$^1$ and R$^2$ independently selected from C$_{1-6}$ alkyl;

$P^1$, $P^2$, $P^3$, and $P^4$ are each independently hydrogen protecting group;

with a source of $^{18}F$ selected from the group consisting of $^{18}F_2$, $^{18}F-CH_3COOF$, and $^{18}F-OF_2$ to give the labelled tracer of formula (II):

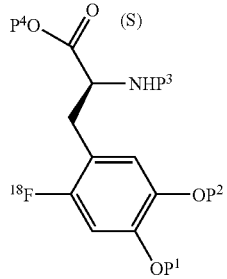

(II)

wherein $P^1$, $P^2P^3$, and $P^4$ are each independently hydrogen or a protecting group; optionally followed by (i) removal of excess fluorinating agent and $^{18}F^-$ ions produced in the generation of the fluorinating agent or in the reaction of a compound of formula (I) with a source of $^{18}F$; and/or (ii) removal of any protecting groups such that $P^1$, $P^2$, $P^3$, and $P^4$ are each hydrogen; and/or (iii) removal of organic solvent; and/or (iv) formulation of the resultant compound of formula (II) as an aqueous solution.

3. A compound of formula (I):

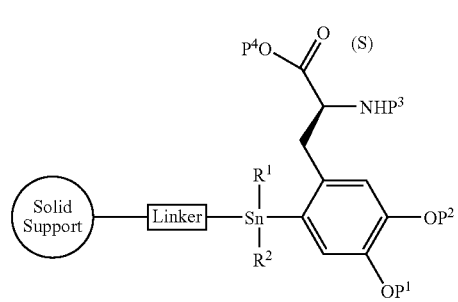

(I)

as defined in claim 1.

4. A compound of formula (Ia):

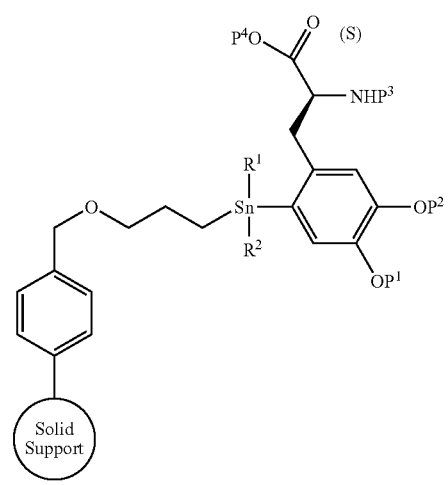

(Ia)

as defined in claim 2.

5. A process for the preparation of a compound of formula (I) as defined in claim 1 which comprises reaction of a compound of formula (III)

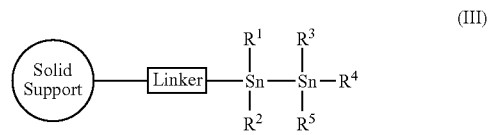

(III)

wherein either $R^1$, $R^2$, $R^3$, $R^4$, and $R^5$ are each independently selected from $C_{1-6}$ alkyl; or $R^1$, $R^2$, $R^3$, and $R^5$ are each independently selected from $C_{1-6}$ alkyl and $R^4$ is

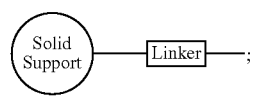

;

with a compound of formula (IV)

(IV)

wherein $P^1$, $P^2$, $P^3$, and $P^4$ are each independently hydrogen or a protecting group.

6. A process according to claim 5 for the preparation of a compound of formula (Ia) which comprises reaction of a compound of formula (IIIa)

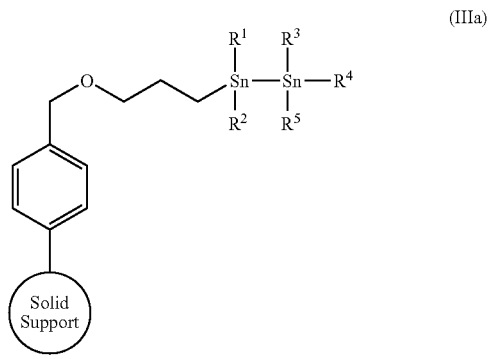

(IIIa)

wherein either $R^1$, $R^2$, $R^3$, $R^4$, and $R^5$ are each independently selected from $C_{1-6}$ alkyl; or $R^1$, $R^2$, $R^3$, and $R^5$ are each independently selected from $C_{1-6}$ alkyl and $R^4$ is

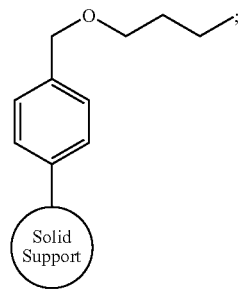

with a compound of formula (IV) as defined in claim 5.

7. A process for the preparation of a compound of formula (V)

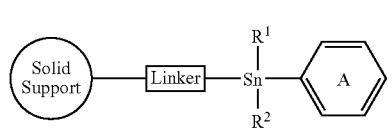
(V)

wherein $R^1$ and $R^2$ are independently $C_{1-6}$ alkyl, and phenyl ring "A" is optionally substituted with 1 to 5 organic groups selected from the group consisting of (a) halo, cyano, hydroxy, $C_{1-6}$ alkoxy, $C_{1-6}$ carboxylic acid or ester, an amine or amide group; and (b) saturated or unsaturated straight or branched chain, or cyclic systems comprising from 1 to 12 carbon atoms and 0 to 4 heteroatoms each of which may be optionally substituted by the groups listed in (a); which comprises:

reaction of a compound of formula (III)

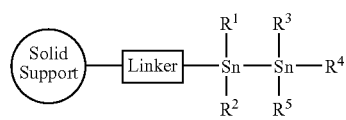
(III)

wherein either:
  $R^1$, $R^2$, $R^3$, $R^4$, and $R^5$ are each independently selected from $C_{1-6}$ alkyl; or
  $R^1$, $R^2$, $R^3$, and $R^5$ are each independently selected from $C_{1-6}$ alkyl and $R^4$ is

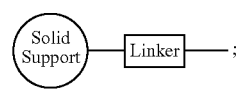

with the corresponding compound of formula (VI)

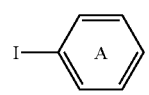
(VI)

wherein phenyl ring "A" is substituted with 1 to 5 organic groups selected from the group consisting of (a) halo, cyano, hydroxy, $C_{1-6}$ alkoxy, $C_{1-6}$ carboxylic acid or ester, an amine or amide group; and (b) saturated or unsaturated straight or branched chain, or cyclic systems comprising from 1 to 12 carbon atoms and 0 to 4 heteroatoms each of which may be optionally substituted by the groups listed in (a).

8. A process according to claim 7 for the preparation of a compound of formula (Va)

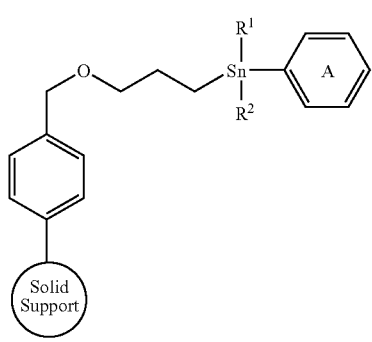
(Va)

wherein $R^1$ and $R^2$ are independently $C_{1-6}$ alkyl and phenyl ring "A" is optionally substituted with 1 to 5 organic groups selected from the group consisting of (a) halo, cyano, hydroxy, $C_{1-6}$ alkoxy, $C_{1-6}$ carboxylic acid or ester, an amine or amide group; and (b) saturated or unsaturated straight or branched chain, or cyclic systems comprising from 1 to 12 carbon atoms and 0 to 4 heteroatoms each of which may be optionally substituted by the groups listed in (a); which comprises:

reaction of a compound of formula (IIIa):

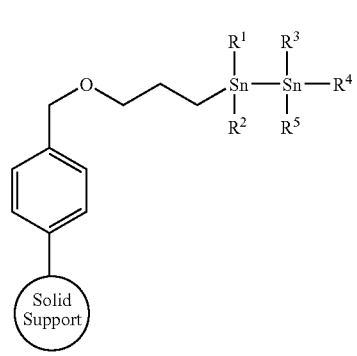
(IIIa)

wherein either $R^1$, $R^2$, $R^3$, $R^4$, and $R^5$ are each independently selected from $C_{1-6}$ alkyl; or
  $R^1$, $R^2$, $R^3$, and $R^5$ are each independently selected from $C_{1-6}$ alkyl and R4 is

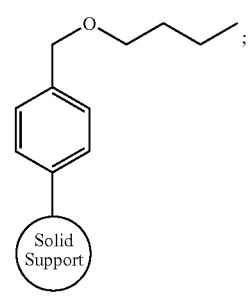

with a compound of formula (VI) as defined in claim 7.

9. A process according to claim 7 wherein the compound of formula (VI) is
2-beta-carbomethoxy-3-beta-(4-iodophenyl)-8-(3-fluoropropyl)-nortropane.

10. A process for the manufacture of a $^{18}$F-labelled tracer of formula (II) as defined in claim 1 for use in PET.

11. A radiopharmaceutical kit for the preparation of $^{18}$F-FDOPA for use in PET, which comprises:
   (i) a vessel containing a compound of formula (I) as defined in claim 1 respectively; and
   (ii) means for eluting the vessel with a source of $^{18}$F; and optionally
   (iii) a cartridge for removal of excess fluorinating agent and $^{18}$F$^-$ ions; and optionally
   (iv) a cartridge for solid-phase deprotection of the resultant product of formula (II) as defined in claim 1.

12. A cartridge for a radiopharmaceutical kit for the preparation of $^{18}$F-FDOPA according to claim 11 for use in PET which comprises:
   (i) a vessel containing a compound of formula (I) as defined in claim 1 respectively; and
   (ii) means for eluting the vessel with a source of $^{18}$F.

13. A method for obtaining a diagnostic PET image which comprises the step of using a radiopharmaceutical kit according to claim 11.

* * * * *